United States Patent
Fujino et al.

(10) Patent No.: US 10,653,708 B2
(45) Date of Patent: May 19, 2020

(54) USES OF ETHER PHOSPHOLIPIDS IN TREATING DISEASES

(71) Applicant: Institute of Rheological Functions of Food, Fukuoka (JP)

(72) Inventors: Takehiko Fujino, Fukuoka (JP); Shiro Mawatari, Fukuoka (JP)

(73) Assignee: Institute of Rheological Functions of Food (JP)

( * ) Notice: Subject to any disclaimer, the term of this patent is extended or adjusted under 35 U.S.C. 154(b) by 0 days.

(21) Appl. No.: 15/625,151

(22) Filed: Jun. 16, 2017

(65) Prior Publication Data
US 2018/0360854 A1 Dec. 20, 2018

(51) Int. Cl.
| | |
|---|---|
| A61K 35/618 | (2015.01) |
| A61K 31/661 | (2006.01) |
| A61K 35/57 | (2015.01) |
| C12P 7/64 | (2006.01) |

(52) U.S. Cl.
CPC .......... *A61K 31/661* (2013.01); *A61K 35/57* (2013.01); *A61K 35/618* (2013.01); *C12P 7/6481* (2013.01); *C12Y 301/01032* (2013.01)

(58) Field of Classification Search
CPC ....... A61K 8/553; A61K 35/57; A61K 35/618
See application file for complete search history.

(56) References Cited

U.S. PATENT DOCUMENTS

| | | | |
|---|---|---|---|
| 9,169,280 B2 * | 10/2015 | Khan | ............... C07F 9/65844 |
| 2010/0029966 A1 | 2/2010 | Fujino et al. | |
| 2010/0055277 A1 | 3/2010 | Nadachi et al. | |
| 2010/0160659 A1 | 6/2010 | Catchpole et al. | |
| 2011/0160471 A1 | 6/2011 | Nadachi et al. | |
| 2012/0283223 A1 | 11/2012 | Ifuku et al. | |
| 2013/0172293 A1 | 7/2013 | Mawatari et al. | |
| 2013/0281404 A1 | 10/2013 | Yazawa et al. | |

FOREIGN PATENT DOCUMENTS

| | | | |
|---|---|---|---|
| EP | 2308954 A1 | | 4/2011 |
| EP | 2522353 A1 | | 11/2012 |
| EP | 3241884 A1 | | 11/2017 |
| JP | 2006124488 A | | 5/2006 |
| JP | 2007262024 | * | 10/2007 |
| JP | 2008179588 A | | 8/2008 |
| JP | 2009227765 A | | 10/2009 |
| JP | 2009263518 A | | 11/2009 |
| JP | 2009538366 A | | 11/2009 |
| JP | 5062873 B2 | | 10/2012 |
| JP | 201353109 A | | 3/2013 |
| JP | 201353110 A | | 3/2013 |
| JP | 5185539 B2 | | 4/2013 |
| JP | 5357005 B2 | | 12/2013 |
| JP | 5430566 B2 | | 3/2014 |
| JP | 5489439 B2 | | 5/2014 |
| JP | 5774816 B2 | | 9/2015 |
| JP | 5847086 B2 | | 1/2016 |
| JP | 6016363 B2 | | 10/2016 |
| JP | 6025568 B2 | | 11/2016 |
| WO | 2008091015 A1 | | 7/2008 |
| WO | 2008146942 A1 | | 12/2008 |
| WO | 2009154309 A1 | | 12/2009 |
| WO | 2010047404 A1 | | 4/2010 |
| WO | 2011083827 A1 | | 7/2011 |
| WO | 2012039472 A1 | | 3/2012 |
| WO | 2016181491 A1 | | 11/2016 |

OTHER PUBLICATIONS

American Brain Tumor Association (ABTA) http://www.abta.org/brain-tumor-information/types-of-tumors/glioma.html?print=t. Accessed Mar. 9, 2016. 3 pages. (Year: 2016).*
Amiri-Kordestani et al. JNCI J Natl Cancer Inst. vol. 104, Issue 8. (2012): 2 pages. (Year: 2012).*
Johnson et al. (Relationships between drug activity and NCI preclinical in vitro and in vivo models and early clinical trials; British Journal of Cancer; (2001) 84 (10), 1424-1431) (Year: 2001).*
Patel et al. ("Schizophrenia: Overview and Treatment Options." Pharmacy and Therapeutics (Sep. 2014); vol. 39 No. 9: pp. 638-645). (Year: 2014).*
UMIN Clinical Trials Registry. "Safety and efficacy of scallop-plasmalogen on patients with primary insomnia:double-blind crossover trial with Polysomnography." Unique ID: UMIN000021337; Receipt No. R000024339. Mar. 4, 2016. (Year: 2016).*
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003). (Year: 2003).*
Clark, Michelle. Pharmacology: VIII. Design and optimization of dosage regimen. Baltimore: Lipincott Williams & Wilkins, 2012. p. 23. (Year: 2012).*
"Anxiety disorders." Mayo Foundation for Medical Education and Research (MFMER). Accessed Jan. 7, 2019. 5 pages. https://www.mayoclinic.org/diseases-conditions/anxiety/symptoms-causes/syc-20350961 (Year: 2019).*
Rodrigues et al. ("Pharmacological interventions for daytime sleepiness and sleep disorders in Parkinson's disease: Systematic review and meta-analysis." Parkinsonism and Related Disorders (2016); 27:25-34). (Year: 2016).*

(Continued)

*Primary Examiner* — Jeffrey S Lundgren
*Assistant Examiner* — Chris E Simmons
(74) *Attorney, Agent, or Firm* — Lerner, David, Littenberg, Krumholz & Mentlik, LLP

(57) ABSTRACT

The present invention relates to uses of ether phospholipids in treating and preventing various diseases, including, but not limited to, neurodegenerative or brain diseases such as Alzheimer's disease, cognitive impairment, brain fatigue, Parkinson disease, depression, anxiety disorder, insomnia and schizophrenia; metabolic syndrome such as diabetes and obesity; various infectious diseases such as viral diseases; diseases related to inflammation; heart diseases, and immune disorders. Preferably, the ether phospholipids are derived from extracting bivalves, which provides superior efficacies in treating and preventing the diseases.

8 Claims, 13 Drawing Sheets

(56) References Cited

OTHER PUBLICATIONS

Mawatari et al., Separation of intact Plasmalogens and all other phospholipids by a single run of high-performance liquid chromatography, Anal. Biochem., May 2007, pp. 54-59, 370.

Ifuku et al., Anti-inflammatory /anti-amyloidogenic effects of plasmalogens in lipopolysaccharide-induced neuroinfflammation in adult mice, Journal of Neuroinflammation, Aug. 2012, pp. 1-13, 9:197.

Katafuchi et al., Effects of Plasmalogens on Systemic Lipopolysaccharide-induced Glial Activation and β-amyloid Accumulation in Adult Mice, Ann. N. Y. Acad. Sci., Jul. 2012, pp. 85-92, 1262.

Oma et al., Changes in Phospholipid Composition of Erythrocyte Membrane in Alzheimer's Disease, Dement Geriatr Cogn Disord Extra, Aug. 2012; pp. 298-303, 2.

Mawatari et al., Dietary plasmalogen increases erythrocyte membrane plasmalogen in rats, Lipids in Health and Disease, Nov. 2012, pp. 1-7, 11:161.

Hossain et al., Plasmalogens Rescue Neuronal Cell Death through an Activation of AKT and ERK Survival Signaling, PLOS ONE, Dec. 2013, pp. 1-14, vol. 8, Issue 12, e83508.

Fujino et al., Efficacy and Blood Plasmalogen Changes by Oral Administration of Plasmalogen in Patients with Mild Alzheimer's Disease and Mild Cognitive Impairment: A Multicenter, Randomized, Double-blind, Placebo-controlled Trial, EBioMedicine, Feb. 2017, pp. 199-205, 17.

Mawatari et al., Simultaneous Preparation of Purified Plasmalogens and Sphingomyelin in Human Erythrocytes with Phospholipases A1 from Aspergillus orizae; Biosci. Biotechnol. Biochem, Dec. 2009, pp. 2621-2625, 73(12).

Chelomin, V.P. et al., Alterations of microsomal lipid synthesis in gill cells of bivalve mollusc Mizuhopecten yessoensis in response to cadmium accumulation, Comparative Biochemistry and Physiology, Part C: Pharmacology, Toxicology & Endocrinology, (1991) pp. 1-5, vol. 99C, No. 1-2.

Chelomin, V.P. et al., Lipid composition and some aspects of aminophospholipid organization in erythrocyte membrane of the marine bivalve mollusc Scapharca broughtoni, Comparative Biochemistry and Physiology, Part B: Biochemistry & Molecular Biology, (1981) pp. 599-604, vol. 69B, No. 3.

Nevenzel, J.C. et al., Plasmalogens in the gill lipids of aquatic animals, Comparative Biochemistry and Physiology, Part B: Biochemistry & Molecular Biology, (1985) pp. 293-297, vol. 82B, No. 2.

Grand, F.L. et al., Membrane phospholipid composition of hemocytes in the Pacific oyster Crassostrea gigas and the Manila clam Ruditapes philippinarum, Comparative Biochemistry and Physiology, Part A: Molecular & Integrative Physiology, Apr. 2011, pp. 383-391, vol. 159A, No. 4.

Misra, S. et al., Naturally occurring etherlinked phosphatidylcholine activates phosphatidylinositol 3-kinase and stimulates cell growth, Journal of Cellular Biochemistry, May 1994, pp. 146-153, vol. 55, No. 1.

Grand, F.L. et al., Altered membrane lipid composition and functional parameters of circulating cells in cockles (*Cerastoderma edule*) affected by disseminated neoplasia, Chemistry and Physics of Lipids, Jan. 2013, pp. 9-20, vol. 167-168.

Kreps, E. et al., Phospholipids in the nervous system of molluscs, Journal of Neurochemistry, Apr. 1968, pp. 285-291, vol. 15, No. 4.

Higashi, S. et al., Role of phospholipids in the aerobic endogenous metabolism of freshwater mussel spermatozoa, Journal of Cellular Physiology, Aug. 1968, pp. 55-63, vol. 72, No. 1.

Hanus, L.O. et al., Plasmalogens, fatty acids and alkyl glyceryl ethers of marine and freshwater clams and mussels, Food Chemistry, Sep. 2009, pp. 491-498, vol. 116, No. 2.

Boselli, E. et al., Characterization of Phospholipid Molecular Species in the Edible Parts of Bony Fish and Shellfish, Journal of Agricultural and Food Chemistry, Feb. 2012, pp. 3234-3245, vol. 60, No. 12.

Kraffe, E. et al., Fatty acids of serine, ethanolamine, and choline plasmalogens in some marine bivalves, Lipids, Jan. 2004, pp. 59-66, vol. 39, No. 1.

Kraffe, E. et al., Cis-4, 7, 10, trans-13-22:4 fatty acid distribution in phospholipids of pectinid species *Aequipecten opercularis* and *Pecten maximus*, Lipids, May 2006, pp. 491-497, vol. 41, No. 5.

Grand, F.L. et al., Disseminated Neoplasia in the Soft-Shell Clam Mya arenaria: Membrane Lipid Composition and Functional Parameters of Circulating Cells, Lipids, Aug. 2014, pp. 807-818, vol. 49, No. 8.

Meneses, P. et al., High resolution 31P NMR of extracted phospholipids, Journal of Lipid Research, May 1988, pp. 679-689, vol. 29, No. 5.

Chebotareva, M.A. et al., Limit of change in unsaturation index of fatty acid composition of phospholipids at adaptation of molluscs to biogenic and abiogenic environmental factors, Journal of Evolutionary Biochemistry and Physiology, Oct. 2011, pp. 448-453, vol. 47, No. 5.

Joh, Y.G. et al., Studies on the lipids of abalone (11) The aldehyde composition of plasmalogen from abalone and some marine molluscs, Bulletin of the Korean Fisheries Society, (1979) pp. 181-189, vol. 12, No. 3.

Yasuda, S., Studies on the Lipids of Japanese Littleneck, Tapes japonica Deshayes. II. Composition of phospholipids, Yukagaku, (1967) pp. 596-600, vol. 16, No. 11.

International Search Report for Application No. PCT/JP2015/063740, dated Jul. 7, 2015.

Fujino et al., Effects of Plasmalogen on Patients with Mild Cognitive Impairment: A Randomized, Placebo-Controlled Trial in Japan, Journal of Alzheimer's Disease and Parkinsonism, Jan. 2018, pp. 1-5, vol. 8.

International Search Report for Application No. PCT/JP2015/063617 dated Jun. 30, 2015.

Yamashita et al., "Preparation of Marine Plasmalogen and Selective Identification of Molecular Species by LC-MS/MS", Journal of Oleo Science, Apr. 9, 2014, vol. 63, No. 5, pp. 423-430.

Supplementary European Search Report and Written Opinion for EP Application No. 15867632, dated May 7, 2018.

Extended European Search Report and Written Opinion for EP Application No. 15891816.9, dated Nov. 28, 2018.

Hara and Radin, "Lipid Extraction of Tissues with a Low-Toxicity Solvent", Analytical Biochemistry, vol. 90, No. 1, Oct. 1978, pp. 420-426.

\* cited by examiner

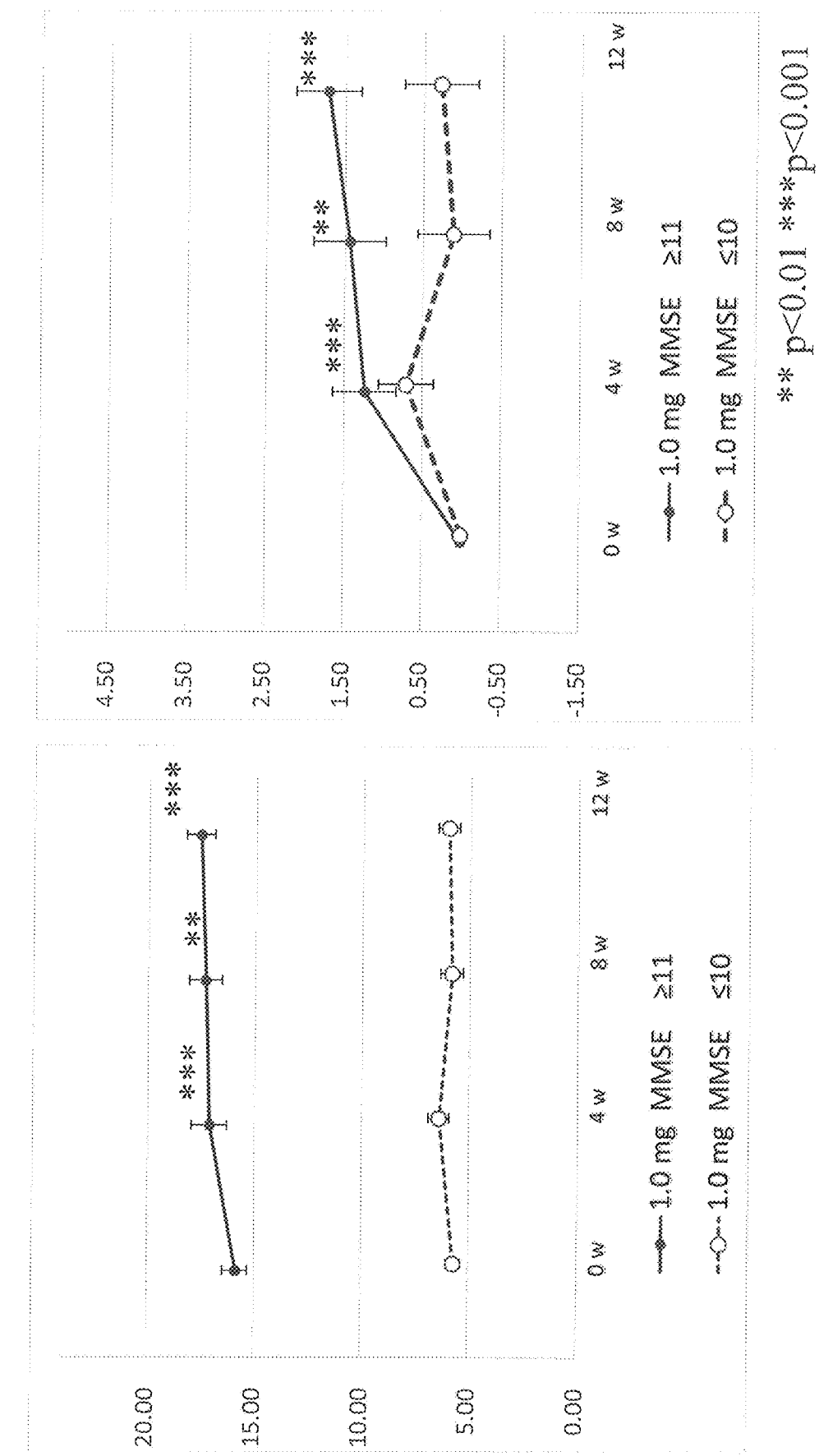

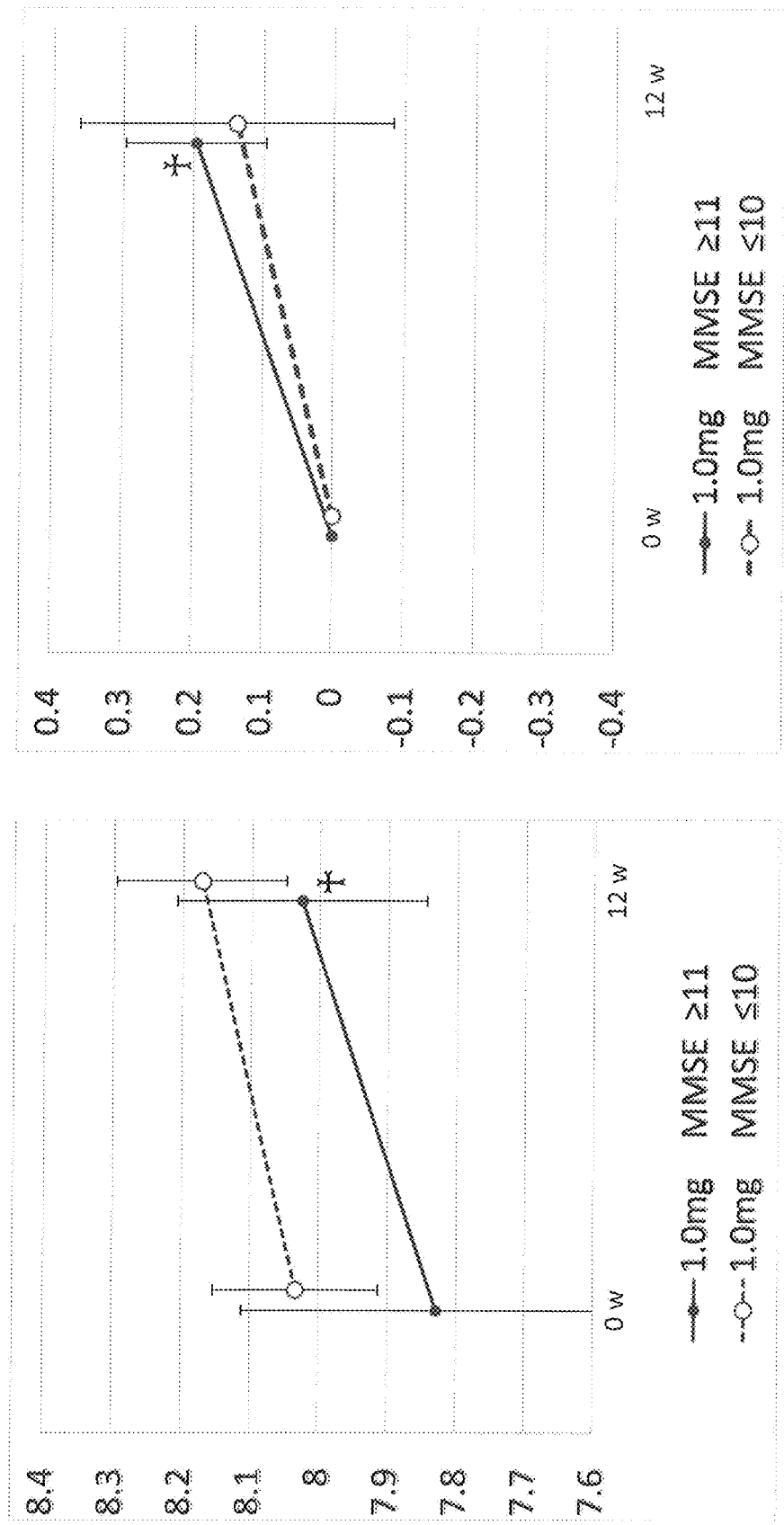

USES OF ETHER PHOSPHOLIPIDS IN TREATING DISEASES

FIELD OF THE INVENTION

The present invention relates to uses of ether phospholipids in treating and preventing various diseases, including, but not limited to, neurodegenerative or brain diseases; metabolic diseases or syndromes; infectious diseases; diseases related to inflammation; heart diseases, and immune disorder. Preferably, the ether phospholipids are derived from extracting bivalves, which provides superior efficacies in treating and preventing the diseases.

BACKGROUND OF THE INVENTION

Lipids refer to substances that have a long fatty acid chain or a similar hydrocarbon chain in a molecule and are present in a living body or derived from a living thing. The lipids may be classified into storage lipids and structural lipids in membranes.

Storage lipids comprise C, H and O, and are generally soluble in organic solvent such as acetone. Triacylglycerol that is a storage lipid is present in a fat tissue of an animal body as energy storage. On the other hand, structural lipids in membranes such as phospholipids comprise a hydrophobic part (fatty acid part) and a hydrophilic part (phosphoric acid and base part) to exhibit amphipathic property. Generally, while storage lipids are soluble in acetone, structural lipids are insoluble in acetone. Such structural lipids are structural components of a biomembrane.

Structural lipids in membranes may be roughly classified into the following categories:

(1) Glycerophospholipids: examples include phosphatidylcholine (lecithin), phosphatidylethanolamine, etc.;
(2) Phosphosphingolipids: examples include sphingomyelin, ceramide ciliatine, etc.;
(3) Glycosphingolipids: examples include cerebroside, sulfatide, ganglioside, etc.; and
(4) Glycoglycerolipids: examples include galactosyldiacylglycerol existing in a microorganism or higher plant.

The above (2) phosphosphingolipids and (3) glycosphingolipids are collectively called as sphingolipids.

Glycerophospholipids is a collective term for phospholipids having a glycerol in their backbone, examples of which include phosphatidylcholine, phosphatidylethanolamine, phosphatidylserine, etc. Many of those glycerophospholipids are bound to a non-polar part (fatty acid part) at the sn-1 position of glycerol backbone by an ester bond (acyl bond), and some are bound at the sn-1 position by a vinyl ether bond (alkenyl bond) or an ether bond (alkyl bond). The former ones bound by a vinyl ether bond are also called as plasmalogens. Glycerophospholipids having a vinyl ether bond and those having an ether bond are collectively called as ether phospholipids.

While phospholipids are integral structural components of a biomembrane, approximately 18% of phospholipids of a mammalian biomembrane are plasmalogens that are vinyl ether phospholipids. In particular, many of plasmalogens are found in brain tissues, cardiac muscles, skeleton muscles, white blood cells and sperms. Many of plasmalogens are bound to polyunsaturated fatty acids such as eicosapentaenoic acid (EPA), docosahexaenoic acids (DHA), arachidonic acids (ARA), and the like at the sn-2 position of glycerol backbone. Therefore, they play not only a role as a reservoir of second messengers for signals between cells such as prostaglandin, leukotriene, etc., but also significant roles as cell fusion, ion transport, etc. In addition, since a vinyl ether bond (alkenyl bond) of plasmalogens is particularly susceptible to oxidative stress, they act as antioxidants at cell membranes.

In mammals, ether phospholipids having an alkyl bond are present although in a small amount. In particular, it is confirmed that phosphatidylcholine and phosphatidylethanolamine having an alkyl bond are present in a rat's brain hippocampus. Furthermore, it is known that ingested phospholipids having an ether bond (alkyl bond) are transformed into plasmalogens in vivo.

These days, it is reported, as shown in WO2011/083827 (Patent Document 1), that plasmalogens-type glycerophospholipids have an effect of brain neurogenesis. In addition, as shown in WO2012/039472 (Patent Document 2) and Ifuku et al., Journal of Neuroinflammation, 9:197 (2012) (Non-patent Document 1), it is reported that plasmalogens-type glycerophospholipids inhibit an increase of glia cells that is considered to be one of the causes triggering a central nervous system inflammation, thereby effective for decreasing central nervous system inflammation, and that they are particularly effective for preventing and treating neurodegenerative disease such as Alzheimer's disease.

It is reported, as shown in, for example, Patent Documents 1-7, that such plasmalogens-type glycerophospholipids may be obtained from a bird tissue such as chicken skin and chicken breast, in an easy manner on a massive scale. Furthermore, Patent Document 8 reports a method for producing ether phospholipids or plasmalogens-type glycerophospholipids from bivalve tissues, and demonstrates that the bivalve extracts produced by such a method are bound to a larger amount of eicosapentaenoic acid (EPA) and docosahexaenoic acid (DHA) at the sn-2 position of glycerol backbone compared to the conventional plasmalogens-type glycerophospholipids derived from chicken tissues.

PRIOR ART DOCUMENTS

Patent Documents

Patent Document 1 WO2011/083827
Patent Document 2 WO2012/039472
Patent Document 3 WO2008/091015
Patent Document 4 WO2008/146942
Patent Document 5 WO2009/154309
Patent Document 6 Japan Patent No. 5,062,873
Patent Document 7 Japan Patent No. 5,185,539
Patent Document 8 WO2016/092878

Non-Patent Documents

Non-patent Document 1 Ifuku et al., Journal of Neuroinflammation, 9:197 (2012)

BRIEF SUMMARY OF THE INVENTION

The present invention relates to uses of ether phospholipids in treating and preventing various diseases.

The present invention provides methods of treating and preventing neurodegenerative or brain diseases; metabolic diseases or syndromes; infectious diseases; diseases related to inflammation; heart diseases, and immune disorders, comprising administering to a subject in need thereof a therapeutically effective amount of ether phospholipids or a composition containing ether phospholipids.

The neurodegenerative or brain diseases include, but are not limited to, Alzheimer's disease, cognitive impairment, brain fatigue, chronic fatigue syndrome, Parkinson disease, depression, anxiety disorder, insomnia and schizophrenia. The metabolic diseases or syndromes include, but are not limited to, diabetes and obesity. The infectious diseases include, but are not limited to, viral diseases, bacterial diseases and prion diseases. The diseases related to inflammation include, but are not limited to, autoinflammatory diseases, collagen diseases and vasculitis. The heart diseases include, but are not limited to, ischemic heart disease, endocarditis, myocarditis, and pericarditis. The immune disorders include, but are not limited to, allergic diseases, autoimmune diseases, immunodeficiency diseases and cancer. Preferably, ether phospholipids can be used for treating diseases including Alzheimer's disease, cognitive impairment, brain fatigue, chronic fatigue syndrome, Parkinson disease, depression, anxiety disorder, insomnia, and obesity. These diseases may be mild, moderate or severe. Alzheimer's disease may include mild Alzheimer's disease, moderate Alzheimer's disease and severe Alzheimer's disease.

The ether phospholipids may be derived from extracting a bird tissue or a bivalve tissue. Preferably, the ether phospholipids are derived from extracting a bivalve tissue, which provides superior efficacies in treating and preventing diseases.

BRIEF DESCRIPTION OF THE DRAWINGS

FIG. 6a depicts the time course mean changes in MMSE score without the baseline effect for the patients with moderate AD and severe AD respectively during 12-week treatment.

FIG. 6b depicts the time course mean changes in MMSE score with the baseline effect for the patients with moderate AD and severe AD respectively during 12-week treatment.

FIG. 12a depicts the mean changes of plasmalogens concentration without the baseline effect in erythrocyte membrane of the patients with moderate AD and severe AD after 12-week treatment.

FIG. 12b depicts the mean changes of plasmalogens concentration with the baseline effect in erythrocyte membrane of the patients with moderate AD and severe AD after 12-week treatment.

DETAILED DESCRIPTION OF THE INVENTION

Figure 1:
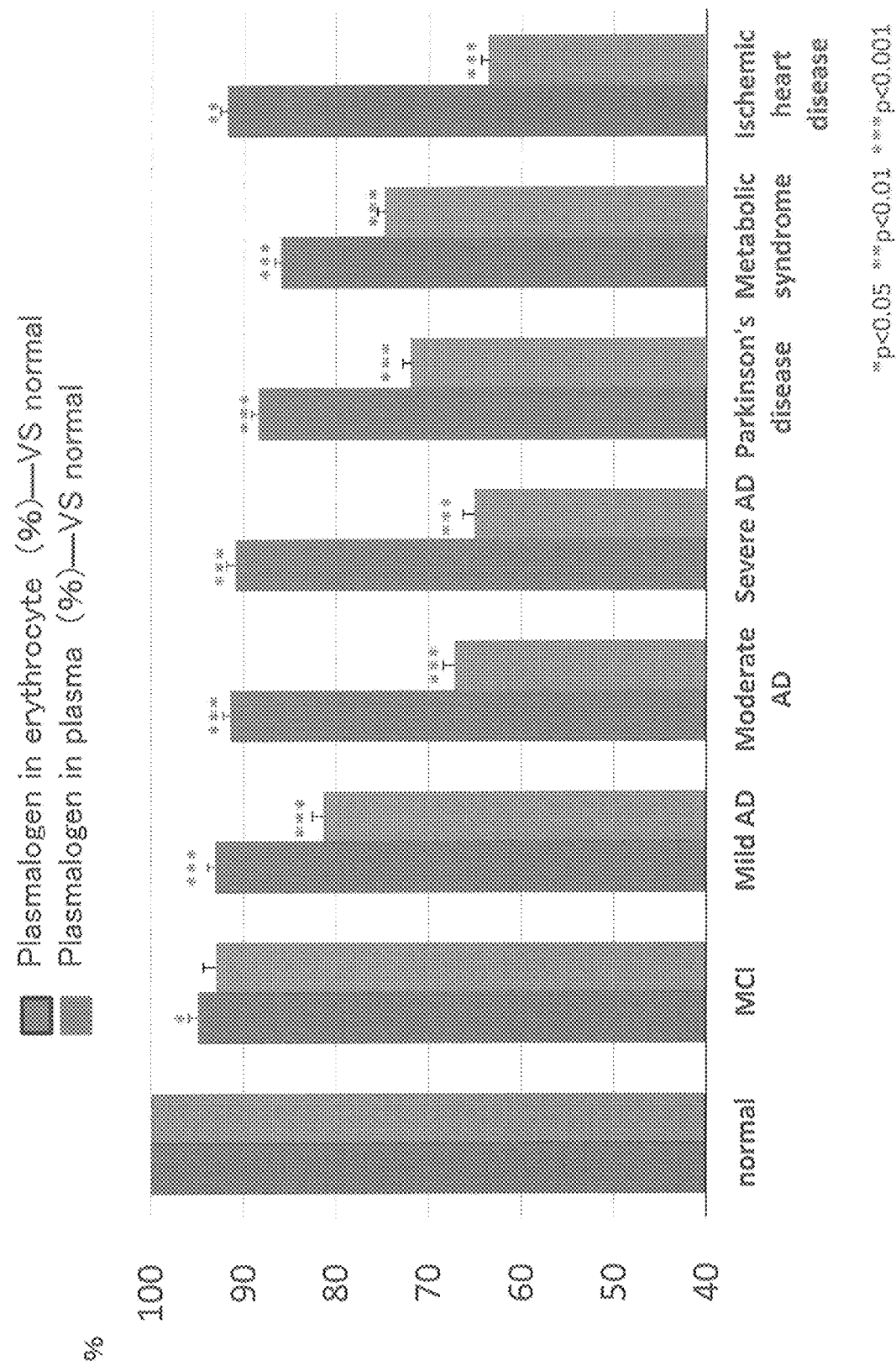
FIG. 1 depicts mean plasmalogen concentrations in erythrocyte membrane and plasma of normal persons and patients with MCI, mild AD, moderate AD, severe AD, Parkinson's disease, metabolic syndrome and ischemic heart diseases.

Before describing at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phrasing and terminology employed herein is for the purpose of description and should not be regarded as limiting.

As used herein, the terms "about," "up to," "generally," "substantially" and the like are intended to mean that slight deviations from absolute are included within the scope of the term so modified. In one embodiment, the terms "about" means a variability of 10% from the reference given, unless otherwise specified.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term "treating" or "treatment" is meant to encompass administering to a subject a compound or composition of the present invention for the purposes of amelioration or elimination of one or more symptoms of a disease or disorder, including palliative care.

The term "preventing" or "prevention" is meant to encompass administering to a subject a compound or composition of the present invention for the purposes of protecting patients or subjects from getting incidence or effects of diseases.

As described herein, "a therapeutically effective amount" of a compound when used for the treatment of a condition is an amount that at least slows the progression of the condition.

Ether phospholipids in the present invention refer to glycerophospholipids that have a vinyl ether bond (alkenyl bond) or an ether bond (alkyl bond) at the 1$^{st}$ position of the glycerol backbone (sn-1). General formulas of ether phospholipids are described as the following Formula (1) and/or (2).

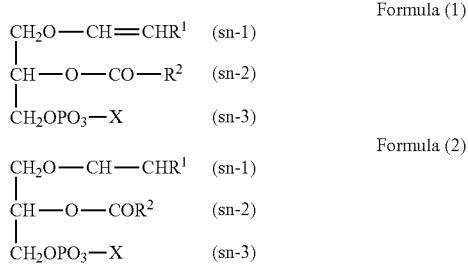

A compound represented by Formula (1) is alkenyl phospholipid (plasmalogens), while a compound represented by Formula (2) is alkyl phospholipid. It is known that ingested ether phospholipids having an ether bond (alkyl bond) are transformed into plasmalogens in vivo. In the present application, the terms "ether phospholipids" and "plasmalogens" may be used exchangeably.

In the above formulas:

$R^1$ represents an aliphatic hydrocarbon group, preferably an aliphatic hydrocarbon group having 14 to 18 carbon numbers, $R^2$ represents an aliphatic hydrocarbon group, which is usually bound to a fatty acid, preferably a polyunsaturated fatty acid, such as eicosapentaenoic acid (EPA), docosahexaenoic acid (DHA), arachidonic acid (ARA), and the like, and more preferably the total amount of these three kinds of fatty acids accounts for 50% or higher of the total fatty acids, and X represents a polar group, preferably ethanolamine, choline, serine, inositol, etc., and more preferably the total amount of ethanolamine and choline account for 90% or higher of the total phospholipids.

In particular, ether phospholipids present in a mammal contain mainly ethanolamine plasmalogens in which X in the above formulas is ethanolamine and choline plasmalogens in which X is choline. Ingested glycerophospholipids having an ether bond (alkyl bond) are absorbed in the original form to be used in each tissue, or are transformed inside a body into alkenyl bond-type phospholipids (plasmalogens).

The ether phospholipids may be derived from extracting a bird tissue or a bivalve tissue. The bird tissue includes, but is not limited to, chicken skin and chicken breast. In a preferred embodiment, the ether phospholipids are derived from extracting a bivalve tissue. The bivalve includes, but is not limited to, a clam, a *corbicula*, a giant clam, a scallop, and an oyster. The bivalve tissue may be an internal organ, a gonad, and muscle.

According to the present invention, the ether phospholipids derived from extracting a bivalve tissue can be obtained through any extraction method.

Preferably, ether phospholipids may be extracted and purified by a method described in WO2016/092878, comprising:

(A) a step of extracting total lipids from bivalve tissues with a mixture of a non-polar organic solvent and a branched alcohol; and (B) a step of reacting the total lipids obtained by the step (A) with phospholipase A1 to hydrolyze diacyl phospholipids mixed therein, followed by solvent partition to get a purified ether phospholipids.

Examples of the non-polar organic solvent include, but are not limited to, saturated fatty hydrocarbons, and preferably are selected from straight-chain saturated hydrocarbons. More preferably, the non-polar organic solvent is hexane.

Examples of the branched alcohol include, but are not limited to, secondary and tertiary alcohols, and preferably are selected from secondary alcohols. More preferably, the branched alcohol is isopropanol.

Preferably, the ratio of the volume of a non-polar organic solvent and the volume of a branched alcohol in the mixture is 3:2.

In one embodiment, phospholipase A1 (PLA1) is used for the hydrolysis. PLA1 specifically hydrolyzes an acyl bond at the sn-1 of diacyl-type phospholipids. Therefore, PLA1 does not act on an ether bond at the sn-1 of ether phospholipids. By the PLA1 processing, diacyl-glycerophospholipids are decomposed into free fatty acids and lyso phospholipids. Free fatty acids and lyso phospholipids may be removed by water based on their nature of being relatively water-soluble.

The PLA1 used is not particularly limited to its derivation, as long as it can attain the above effect. The exemplary PLA1 may be the one derived from *Aspergillus orizae*. Such PLA1 may be purchased from Mitsubishi Kagaku Foods Corporation.

The amount of the PLA1 used may be selected as deemed fit, depending on the amount of the total glycerophospholipids. The amount of the PLA1 used per 1 g of the total glycerophospholipids is preferably about 0.15-0.45 g, more preferably about 0.2-0.3 g.

The enzymatic hydrolysis reaction by PLA1 may be performed in a buffer. Such a buffer may be selected as deemed fit depending on the PLA1 used. For example, 0.1M citric acid-HCl buffer (pH 4.5) may be used. In that case, the total glycerophospholipids may be dissolved by adding the buffer, and subsequently PLA1 may be added.

Although there is no particular restriction as to the amount of the buffer used herein as long as that the enzymatic hydrolysis reaction by PLA1 can be progressed, the volume of the buffer used per 1 g of the total glycerophospholipids is preferably about 1-30 mL, more preferably about 5-15 mL.

The reaction conditions of the enzymatic hydrolysis, such as temperature, reaction time and pH, can be selected as deemed fit. The reaction is run preferably at the temperature of about 30-70° C., more preferably at about 45-55° C., and most preferably at about 50° C. Stirring is preferably provided during the reaction. The reaction time is preferably about 1-5 hours, and more preferably about 1-2 hours. The pH is preferably at about 3.5-5.5, and more preferably at about 4-5.

The enzymatic hydrolysis reaction by PLA1 may be stopped by cooling.

In addition, subsequent to the hydrolysis reaction, deactivation treatment of PLA1 may be performed. For example, the deactivation treatment may be performed by increasing the temperature to around 70° C.

By the above step (B), a resulting liquid from the hydrolysis process may be obtained wherein diacyl phospholipids are decomposed. In one embodiment, to the hydrolysis resulting liquid is added hexane-isopropanol mixture (3:2) that is diluted by 5-10 times. The resulting mixture is placed into a separating funnel. Water in an amount of ⅔ of the volume of the resulting mixture is then added. Hexane layer (the upper layer) is separated and dried to a resulting solid. By doing so, a lipid decomposed product (free fatty acid and lyso phospholipid), enzyme protein, and enzyme buffer may be removed by water.

In one embodiment, in order to further remove remained neutral fat, the resulting solid is treated with acetone. After mixing, the resulting mixture was kept in an ice bath for 30 mines, and then centrifuged to collect precipitates to obtain purified bivalve-derived ether phospholipids.

Ether phospholipids are useful in treating and preventing various diseases, including, but not limited to, neurodegenerative or brain diseases; metabolic diseases or syndromes; infectious diseases; diseases related to inflammation; heart diseases, and immune disorders. The neurodegenerative or brain diseases include, but are not limited to, Alzheimer's disease, cognitive impairment, brain fatigue, chronic fatigue syndrome, Parkinson disease, depression, anxiety disorder, insomnia and schizophrenia. The metabolic diseases or syndromes include, but are not limited to, diabetes and obesity. The infectious diseases include, but are not limited to, viral diseases, bacterial diseases and prion diseases. The diseases related to inflammation include, but are not limited to, autoinflammatory diseases, collagen diseases and vasculitis. The heart diseases include, but are not limited to, ischemic heart disease, endocarditis, myocarditis, and pericarditis. The immune disorders include, but are not limited to, allergic diseases, autoimmune diseases, immunodeficiency diseases and cancer.

Brain fatigue refers to disruption or collapse of relationship among neocortex, limbic system and diencephalon. It also means relationship failure between left brain and right brain. In other words, intercellular or intertissual relationship is the most important, although abnormality in each cell or each tissue matters.

Chronic fatigue syndrome (CFS), is a medical condition characterized by long-term fatigue and other symptoms that limit a person's ability to carry out ordinary daily activities. Quality of life of persons with CFS can be compromised. Biological, genetic, infectious, and psychological mechanisms have been proposed, but the cause is not fully understood. CFS is understood that it is not due to ongoing exertion or other medical conditions, and cannot be relieved by rest. Diagnosis is based on a person's signs and symptoms.

Anxiety disorders are a group of mental disorders characterized by feelings of anxiety and fear. These feelings may cause physical symptoms, such as a fast heart rate and shakiness. There are a number of anxiety disorders: including generalized anxiety disorder, specific phobia, social anxiety disorder, separation anxiety disorder, agoraphobia, panic disorder, and selective mutism. The disorder differs by what results in the symptoms. Patients often have more than one anxiety disorder.

Ether phospholipids are preferably useful in treating and preventing Alzheimer's disease, cognitive impairment, brain fatigue, chronic fatigue syndrome, Parkinson disease, depression, anxiety disorder, insomnia, and obesity. These diseases may be mild, moderate or severe. Alzheimer's disease includes mild Alzheimer's disease, moderate Alzheimer's disease and severe Alzheimer's disease.

Ether phospholipids derived from bivalve tissues are bound to a larger amount of eicosapentaenoic acid (EPA) and docosahexaenoic acid (DHA) at the sn-2 position of glycerol backbone compared to the conventional plasmalogens-type glycerophospholipids derived from chicken tissues.

Such structures enable ether phospholipids derived from bivalve tissues to be significantly effective for treating and preventing various diseases, including, but not limited to, neurodegenerative or brain diseases comprising Alzheimer's disease, cognitive impairment, brain fatigue, chronic fatigue syndrome, Parkinson disease, depression, anxiety disorder, insomnia and schizophrenia; metabolic diseases and syndromes such as diabetes and obesity; infectious diseases comprising viral diseases, bacterial diseases and prion diseases; diseases related to inflammation comprising autoinflammatory diseases, collagen diseases and vasculitis; heart diseases comprising ischemic heart disease, endocarditis, myocarditis, and pericarditis, and immune disorders comprising allergic diseases, autoimmune diseases, immunodeficiency diseases and cancer. Preferably, ether phospholipids derived from bivalve tissues are useful in treating and preventing Alzheimer's disease, cognitive impairment, brain fatigue, chronic fatigue syndrome, Parkinson disease, depression, anxiety disorder, insomnia, and obesity. Alzheimer's disease includes mild Alzheimer's disease, moderate Alzheimer's disease and severe Alzheimer's disease.

The present invention provides methods of treating and preventing neurodegenerative or brain diseases comprising Alzheimer's disease, cognitive impairment, brain fatigue, chronic fatigue syndrome, Parkinson disease, depression, anxiety disorder, insomnia and schizophrenia; metabolic diseases or syndrome such as diabetes and obesity; infectious diseases such as viral diseases, bacterial diseases and prion diseases; diseases related to inflammation comprising autoinflammatory diseases, collagen diseases and vasculitis; heat diseases comprising ischemic heart disease, endocarditis, myocarditis, and pericarditis, and immune disorders comprising allergic diseases, autoimmune diseases, immunodeficiency diseases and cancer, comprising administering to a subject in need thereof a therapeutically effective amount of ether phospholipids or a composition containing ether phospholipids. Preferably, the present invention provides methods of treating and preventing Alzheimer's disease, cognitive impairment, brain fatigue, chronic fatigue syndrome, Parkinson disease, depression, anxiety disorder, insomnia, and obesity, comprising administering to a subject in need thereof a therapeutically effective amount of ether phospholipids or a composition containing ether phospholipids.

The ether phospholipids for treatment of such diseases may be derived from extracting a bird tissue or a bivalve tissue. Preferably, the ether phospholipids are derived from extracting a bivalve tissue, which provides superior efficacies in treating and preventing diseases. Preferably, the ether phospholipids are useful in treating diseases selected from the group consisting of Alzheimer's disease, cognitive impairment, brain fatigue, chronic fatigue syndrome, Parkinson disease, depression, anxiety disorder, insomnia, or obesity.

Ether phospholipids may be contained in a composition including, but not limited to, a beverage, a food, and a pharmaceutical composition. The exemplary form of beverage and food products includes a sweet (such as frozen dessert, jelly, cake, candy, chewing gum, juice, syrup, etc.), bread, dairy product such as milk, yogurt, etc., and other various products. Pharmaceutical compositions useful herein contain ether phospholipids in a pharmaceutically acceptable carrier optionally with other pharmaceutically inert or inactive ingredients.

The compositions containing the ether phospholipids may be formulated neat or with one or more carriers for administration. The type and amount of the carrier(s) are determined by chosen route of administration and type of composition, and may be readily selected by one of skill in the art. The carriers may be in dry or liquid form and must be physiologically compatible and/or pharmaceutically acceptable. Examples of carriers include, without limitation, wetting agents, dispersion assistants, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. Pharmaceutically acceptable liquid carriers may include, e.g., DMSO, saline, buffered saline, hydroxypropylcyclodextrin, and mixtures thereof. A variety of solid carriers are known to those of skill in the art, which include excipients (lactose, sucrose, dextrin, starch, etc.), disintegrant (starch, calcium carbonate, carboxymethylcellulose calcium, carboxymethylcellulose sodium, starch, corn starch, alginate sodium, etc.), binder (starch, gum arabic, gelatin, carboxymethylcellulose, polyvinylpyrrolidone, hydroxypropylcellulose, etc.) or lubricant (talc, magnesium stearate, sodium stearate, polyethyleneglycol 6000, etc.) and the like.

The ether phospholipids may be administered by any route, taking into consideration the specific condition for which it has been selected. In some embodiments, the ether phospholipids can be administered as beverage or food products. In some embodiments, such products may be formulated as tablets (including sugar-coated tablet, and film-coated tablet), powders, pills, capsules, or a liquid. In certain embodiments, the ether phospholipids can be administered as pharmaceutical compositions. Such compositions may be formulated for intravenous administration, subcutaneous administration, oral administration, rectal administration, parenteral, intravitreal administration, intramuscular administration, intranasal administration, dermal administration, topical administration, or sublingual administration. In some embodiments, such compositions are formulated as tablets (including sugar-coated tablet, and film-coated tablet), powders, pills, capsules (including hard or soft gelatin capsules), a liquid, a suppository, a solution, a gel, an emulsion, or an ointment. In addition, as deemed necessary, coating may be provided by a publicly known measure for the purposes of taste masking, enteric function or long-acting function.

Liquid compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the ether phospholipids are dissolved a liquid carrier. In another embodiment, the ether phospholipids are suspended in a liquid carrier. The ether phospholipids may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the ether phospholipids. For example, the unit dosage can be packaged compositions, e.g., packaged powders, vials, ampoules, prefilled syringes or sachets containing liquids.

The amount or dosage of the ether phospholipids to achieve a therapeutic effect will depend on the age, weight, sex, physical condition, and morphology of the patient; formulation of the composition, route of delivery and frequency of administration. It is also contemplated that the amount or dosage of the ether phospholipids may be administered in unit dosage form and that one skilled in the art would adjust the unit dosage form accordingly to reflect the relative level of activity. The decision as to the particular amount or dosage to be employed (and the number of times to be administered per day) is within the discretion of the ordinarily-skilled physician, and may be varied by titration of the amount or dosage to the particular circumstances to produce the desired therapeutic effect. In one embodiment, the therapeutically effective amount is about 0.01 mg/kg to about 10 mg/kg body weight, preferably about 0.2 mg/kg to about 10 mg/kg body weight per day. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.2 mg/kg, about 0.1 mg/kg, about 100 µg/kg, about 75 µg/kg, about 50 µg/kg, about 25 µg/kg, about 10 µg/kg, or about 1 µg/kg. For an average adult, the amount may be about 0.25 mg to about 1,000 mg per dosage, preferably 0.5 mg to about 20 mg per dosage, and more preferably about 0.5 mg to about 1 mg per dosage. However, the therapeutically effective amount of the ether phospholipids can be determined by the attending physician and depends on the condition treated; the route of delivery; the age, weight, and severity of the patient's symptoms; and response pattern of the patient.

The therapeutically effective amounts of the ether phospholipids may be provided on regular schedule, i.e., daily, weekly, monthly, or yearly basis or on an irregular schedule with varying administration days, weeks, months, etc. Alternatively, the therapeutically effective amounts to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner.

Although it is easy and convenient to use the ether phospholipids by mixing them into any products, a certain amount of the ether phospholipids is required to achieve the effects of treating and preventing various diseases. For example, a beverage and food product contains the ether phospholipids preferably in the amount of approximately 0.01-80 mass %, more preferably in the amount of approximately 0.05-20 mass %.

EXAMPLES

The followings describe the present invention with reference to examples in details. However, the present invention is not limited to these examples.

Example 1

Correlation Between the Severity of the Diseases and the Concentration of Blood Plasmalogens
Outcome Measurements:
Mini Mental State Examination (MMSE): MMSE is a set of questions developed by Folstein in 1975 in the United States for diagnosing dementia. The test comprises 11 questions and the perfect score is 30-point, covering faculty of orientation, memory skill, calculation ability, language ability, ability on pictorial figure, and the like. 24-point or higher score indicates a normal cognition. Below this, scores can indicate severe (less than 10-point) and moderate (less than 20-point) cognitive impairment. MMSE-J is the Japanese version of MMSE.
Wechsler Memory Scale-Revised (WMS-R): WMS-R is a memory test that is used internationally. The test can measure various aspects of memory functions, effective to assess diseases related to memory deficits such as dementia. It comprises questions using languages and questions using pictorial figures. In the present invention, "Verbal Memory" and "Delayed Memory," which are what "General Memory" is segmentalized, were tested.
Geriatric Depression Scale (GDS): GDS is a screening test for depression symptom in elderly-aged people, and GDS-S-J is the revised on for Japanese.
Selection of Patients:
Mild Cognitive Impairment (MCI): The patient who has 23<MMSE<27
Mild Alzheimer's diseases (AD): The patient who has 20≤MMSE≤23
Moderate AD: The patient who has 11≤MMSE<20
Severe AD: The patient who has MMSE≤10
Metabolic diseases or syndromes: The patient with diabetes, high blood pressure, and/or brain fatigue.
Procedure:
Blood samples were collected from the normal elderly and the patients with MCI, mild AD, moderate AD, severe AD, Parkinson's disease, metabolic syndrome, and ischemic heart diseases, and the concentration of plasmalogens in their erythrocyte membrane and plasma was measured. The results of the mean plasmalogens concentration in the normal elderly and the patients were shown in FIG. 1. The plasmalogens concentration of normal elderly is expressed as 100% and those of patients with various diseases are expressed as the ratio of normal elderly.
Results:
FIG. 1 demonstrates that the patients with MCI, mild AD, moderate AD, severe AD, Parkinson's disease, metabolic syndrome and ischemic heart diseases have lower plasmalogens concentration in erythrocyte membrane and plasma, and in particular, in plasma, comparing to the normal persons. The more severe the disease is, the lower the plasmalogens concentration is.

Example 2

Figures 2A, 2B:
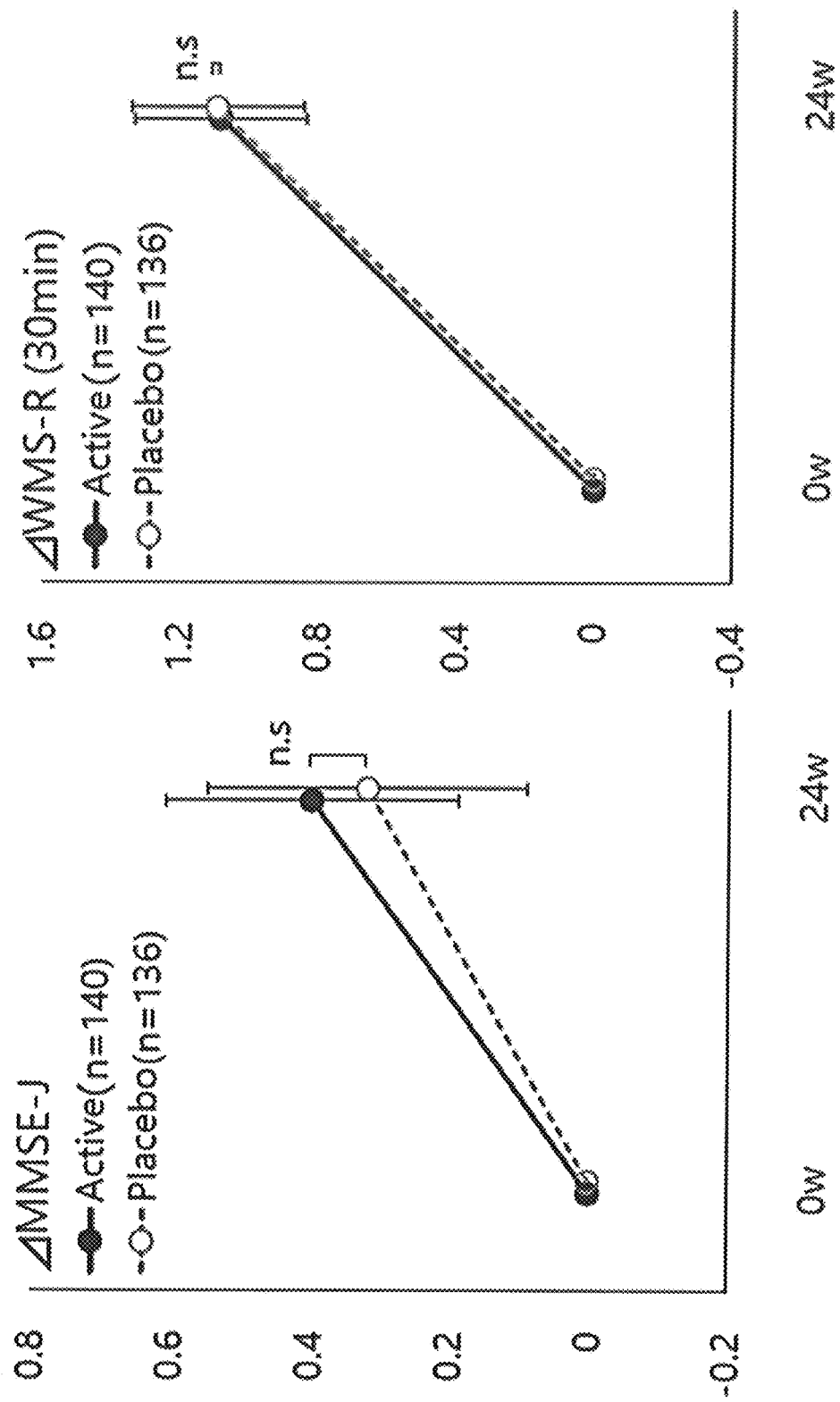
FIG. 2a depicts the mean changes in MMSE-J after receiving plasmalogens extracted from scallop or placebo for the patients after 24-week treatment.
FIG. 2b depicts the mean changes in WMS-R measured 30 minutes after receiving plasmalogens extracted from scallop or placebo for the patients after 24-week treatment.
Figures 3A, 3B:
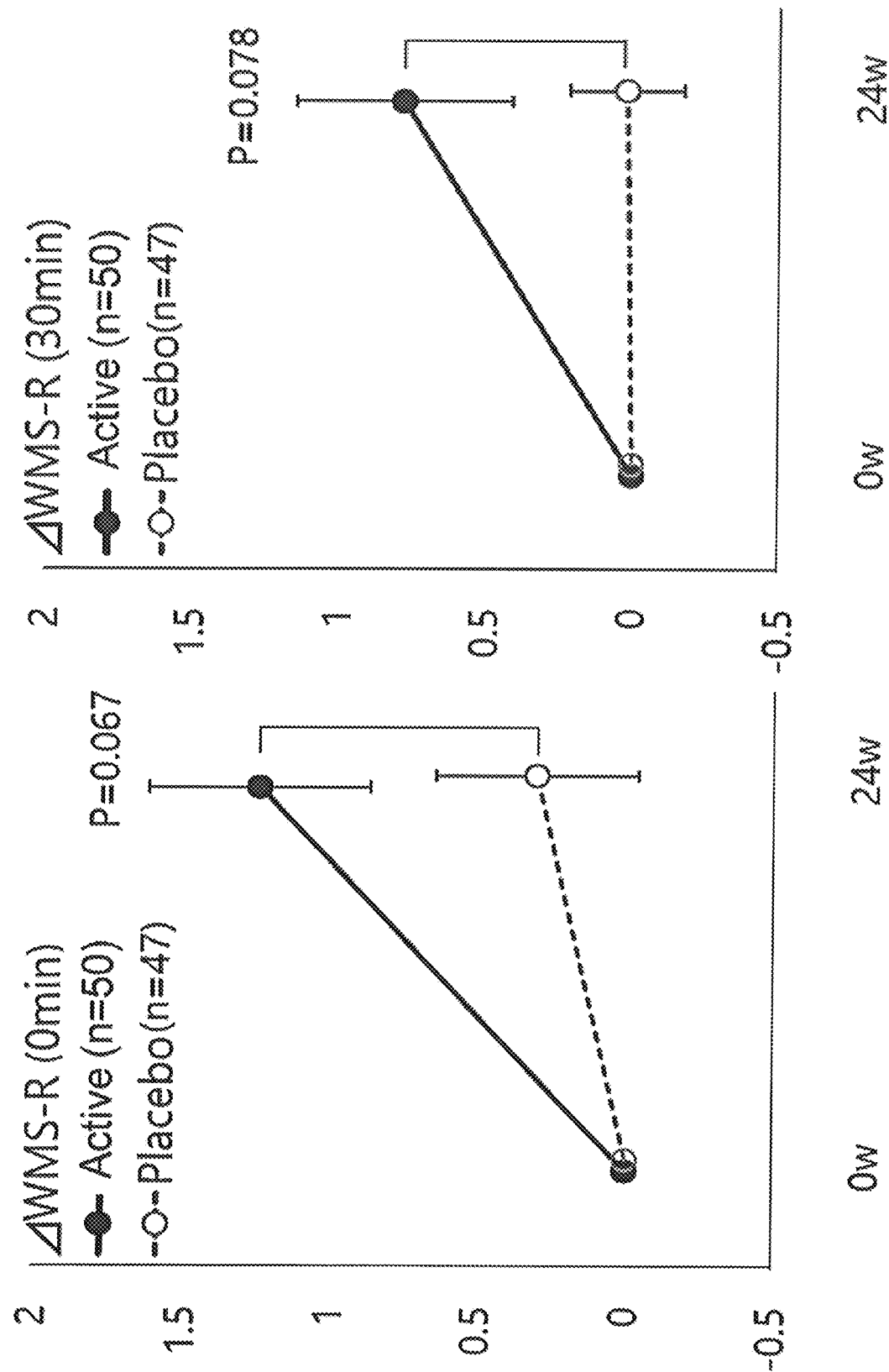
FIG. 3a depicts the mean changes in WMS-R measured immediately after receiving plasmalogens extracted from scallop or placebo for the patients having mild AD after 24-week treatment.
FIG. 3b depicts the mean changes in WMS-R measured 30 minutes after receiving plasmalogens extracted from scallop or placebo for the patients having mild AD after 24-week treatment.
Figures 4A, 4B:
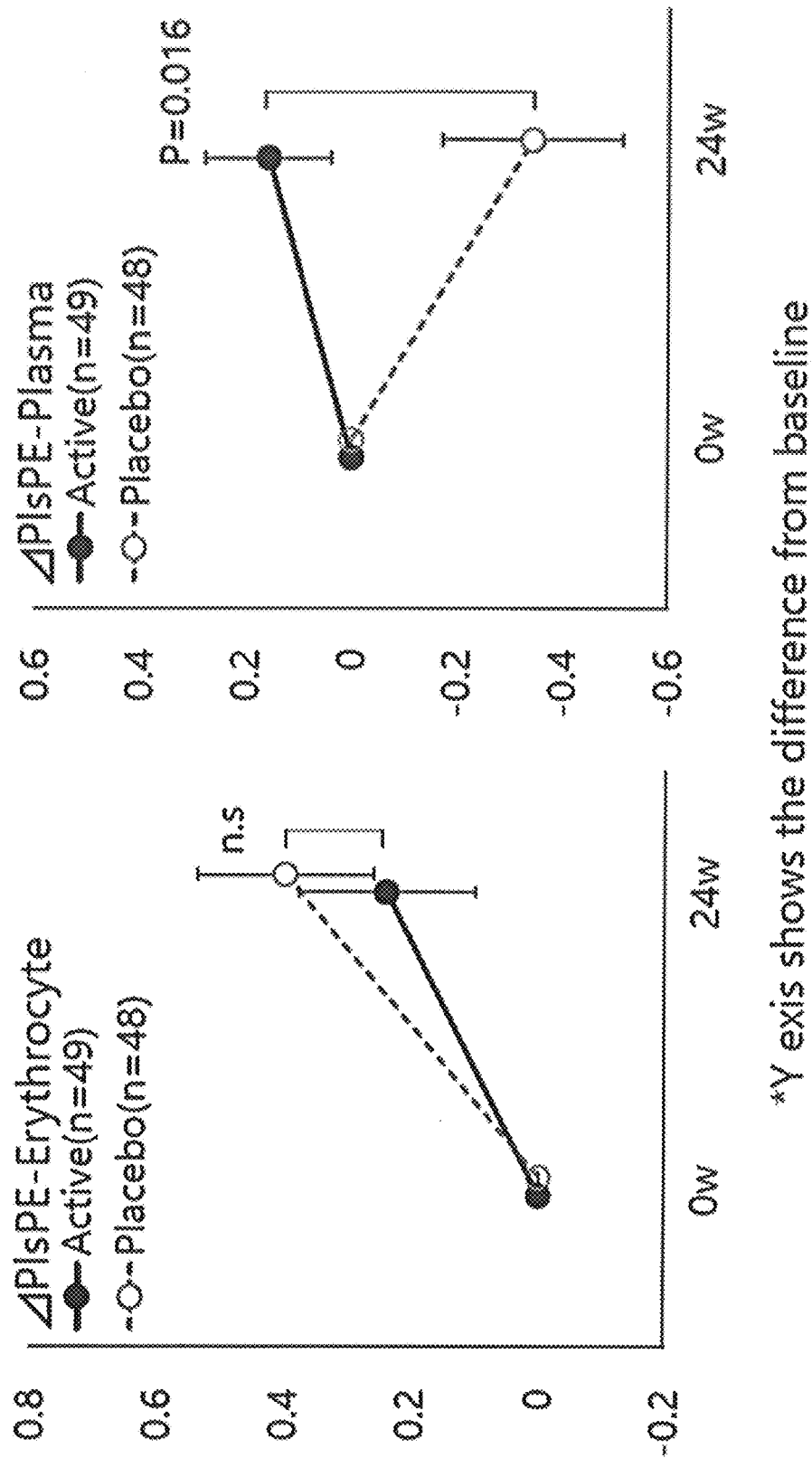
FIG. 4a depicts the mean changes of plasmalogens (Pl-sPE) concentration in erythrocyte membrane after receiving plasmalogens extracted from scallop or placebo for the patients with mild AD after 24-week treatment.
FIG. 4b depicts the mean changes of plasmalogens (Pl-sPE) concentration in plasma after receiving plasmalogens extracted from scallop or placebo for the patients with mild AD after 24-week treatment.

Efficacy of Plasmalogens Extracted from Scallop in the Treatment of Mild AD and Mild MCI
328 patients aged 60-85 years old, who showed 20-27 in MMSE-J score, participated. They were randomized to orally receive either 1 mg/day plasmalogens extracted from scallop or placebo for 24 weeks. 276 patients completed the study. No clinically significant side effects were observed.
The mean changes in MMSE-J and WMS-R (30 min) (measured 30 minutes after receiving plasmalogens extracted from scallop or placebo) after 24-week treatment for all the patients were shown in FIG. 2a and FIG. 2b, respectively. MMSE-J score improved more in the active group compared to the placebo group, but the difference between the two groups did not reach significance. WMS-R score improved in both groups, but the difference between the two groups was not significant.
All patient subjects were classified into two subgroups of patients having mild AD and MCI, respectively. The mean changes in WMS-R (0 min) and WMS-R (30 min) after 24-week treatment for patients having mild AD, measured immediately and 30 minutes after receiving plasmalogens extracted from scallop or placebo were shown in FIG. 3a and FIG. 3b, respectively. Both WMS-R (0 min) and WMS-R (30 min) scores improved more in the active group compared to the placebo group, and the significant difference between the two groups were observed (p is 0.067 and 0.078, respectively).
This indicated that oral administration of plasmalogens extracted from scallop improved memory functions in patients with mild AD and MCI.
Changes of the Concentration of Plasmalogens in Patients with Mild AD after Oral Administration of Plasmalogens Extracted from Scallop
The mean changes of plasmalogens (PlsPE) concentration in erythrocyte membrane and plasma of the patients with mild AD after 24-week treatment were shown in FIG. 4a and FIG. 4b, respectively. Plasmalogens in plasma was significantly decreased for the placebo group while it was increased for the active group at the end point, and the significant difference between these two groups was observed (p is 0.016).

Example 3

Figure 5B:
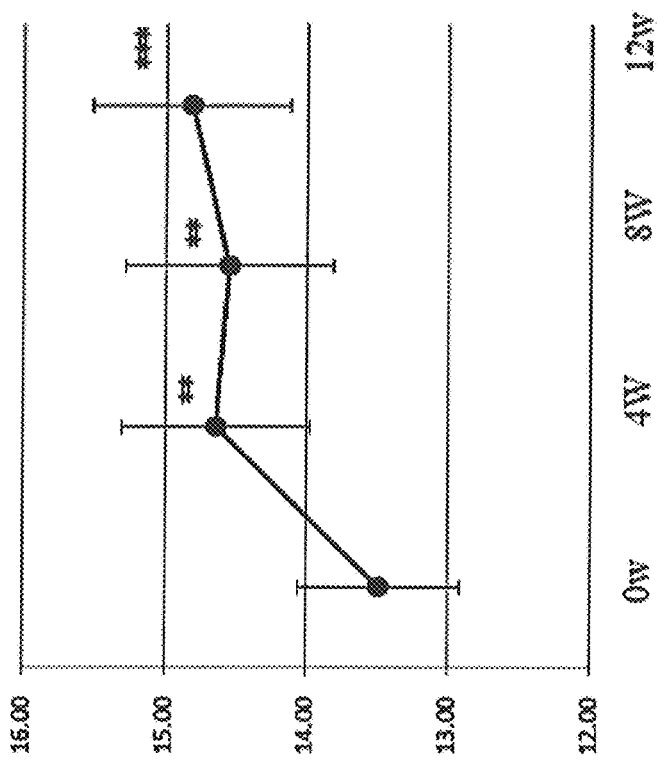
FIG. 5b depicts the time course changes in MMSE score with the baseline effect for the patients with moderate AD and severe AD during 12-week treatment.
Figure 5A:
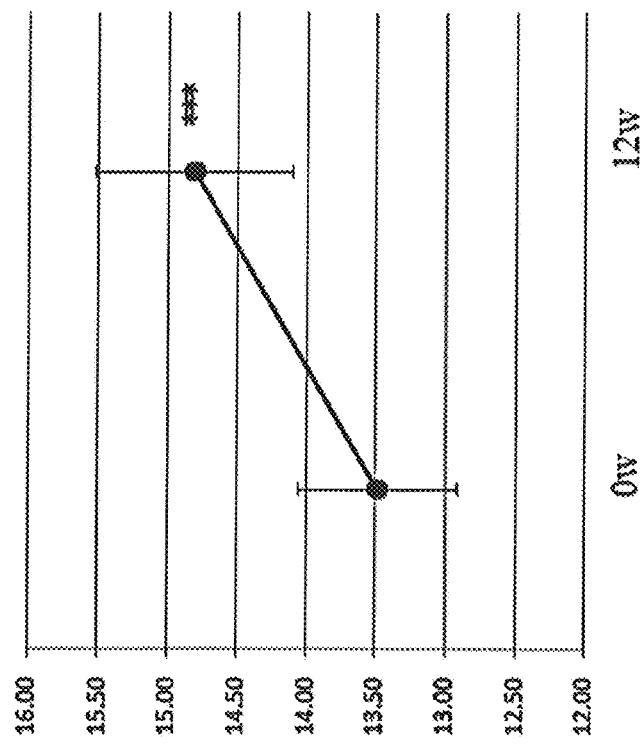
FIG. 5a depicts the mean changes in MMSE score without the baseline effect for the patients with moderate AD and severe AD after 12-week treatment.

Efficacy of Plasmalogens Extracted from Scallop in the Treatment of Moderate to Severe AD
Total 75 patients with 58 patients who showed 11-20 in MMSE-J score (moderate AD) and 17 patients who showed less than 11 in MMSE-J score (severe AD) participated. They received orally 1 mg/day plasmalogens extracted from scallop for three months. No clinically significant side effects were observed.
The mean changes in MMSE score without the baseline effect after 12-week treatment for all the patients with moderate AD and severe AD were shown in FIG. 5a. The time course mean changes in MMSE score with the baseline effect during 12-week treatment for all the patients with moderate AD and severe AD were shown FIG. 5b. The time course mean changes in MMSE score without and with the baseline effect during 12-week treatment for the patients with moderate AD and severe AD were shown in FIG. 6a and FIG. 6b, respectively.

Figure 7:
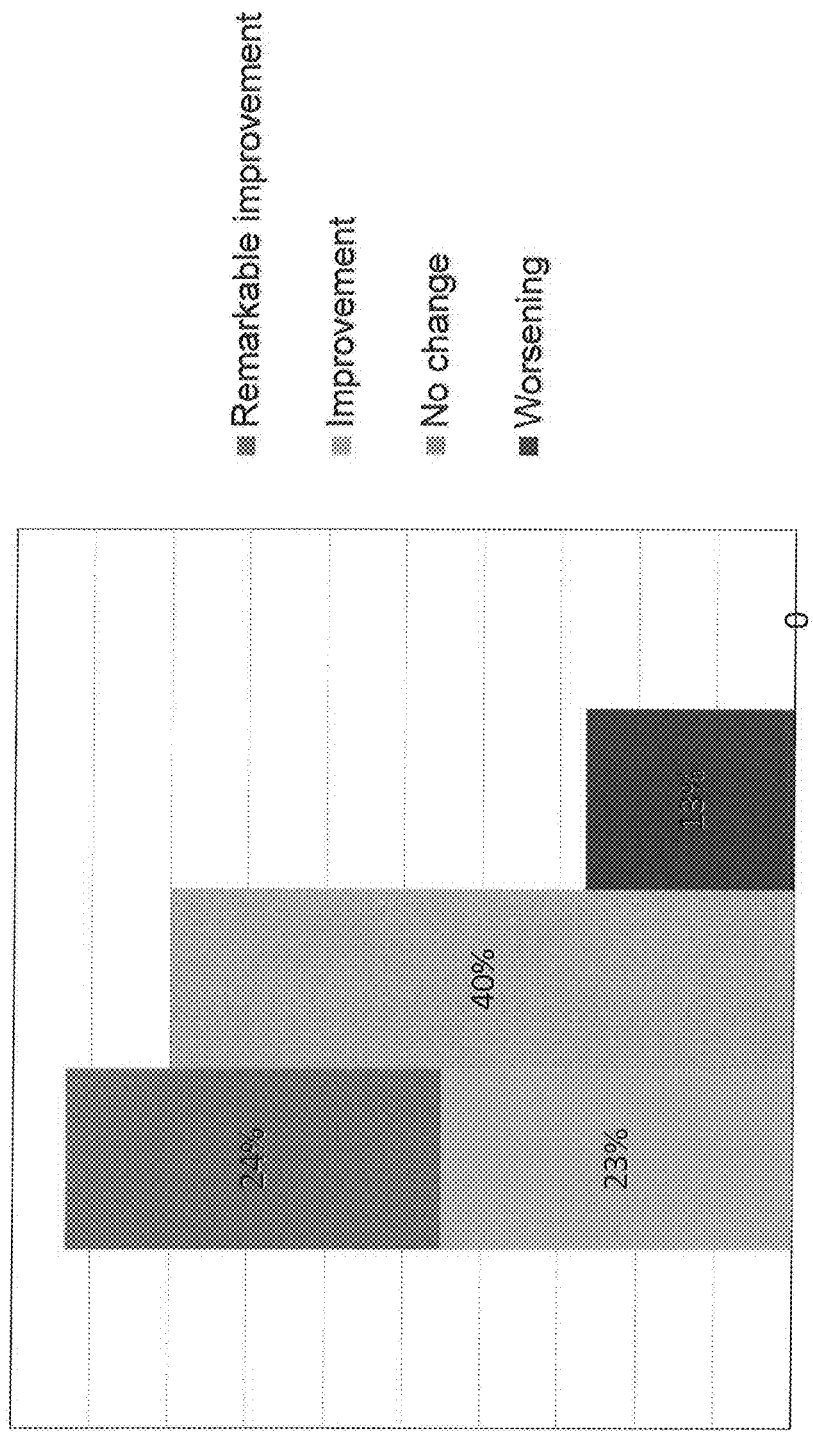
FIG. 7 depicts the mean MMSE changes for the patients with moderate AD and severe AD after three-month oral administration of plasmalogens extracted from scallop.
Figures 8A, 8B:
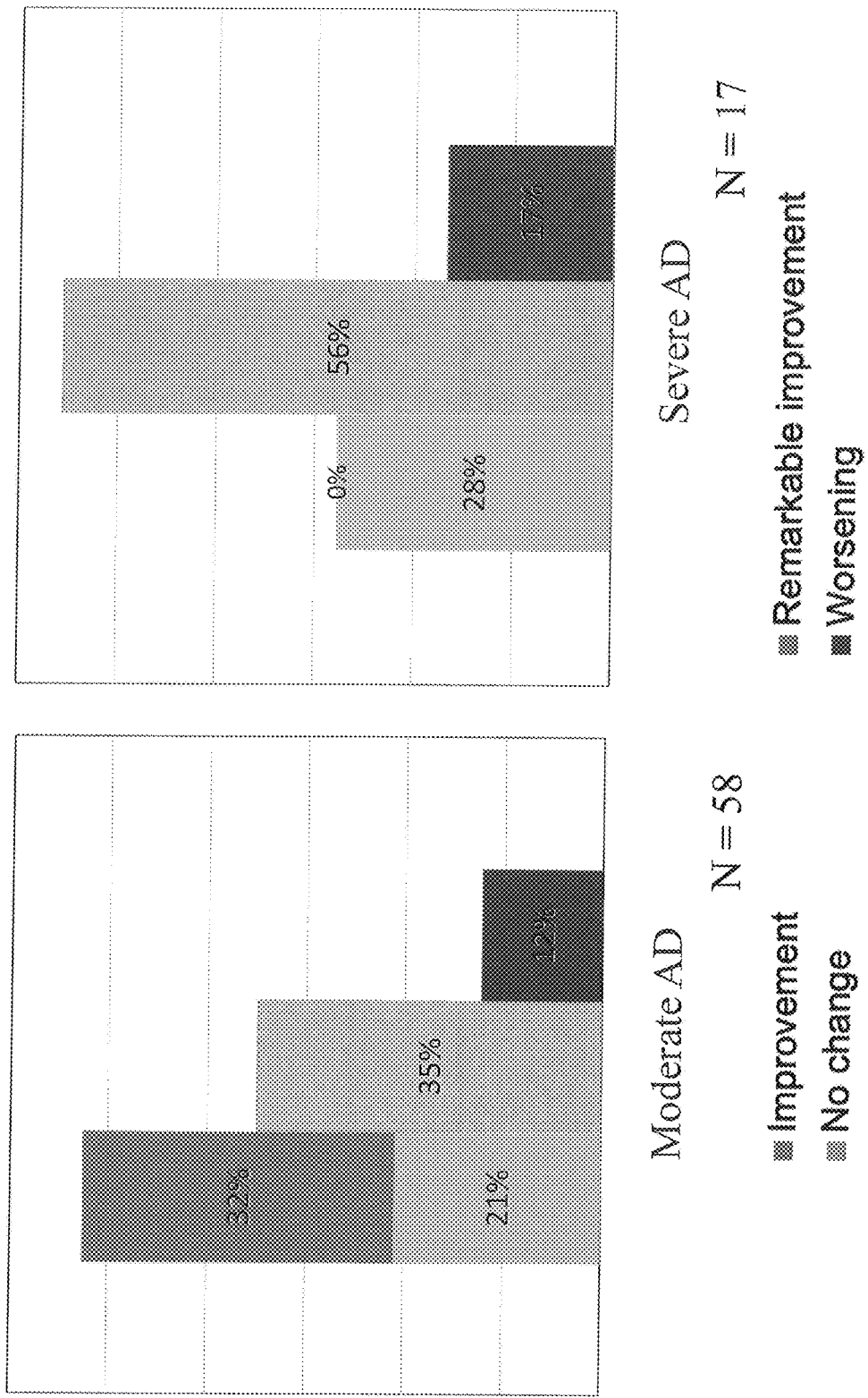
FIG. 8a depicts the mean MMSE changes for the patients with moderate AD after three-month oral administration of plasmalogens extracted from scallop.
FIG. 8b depicts the mean MMSE changes for all the patients with severe AD after three-month oral administration of plasmalogens extracted from scallop.

The mean MMSE changes for the total 75 patients, 58 patients with moderate AD and 17 patients with severe AD after three-month oral administration of plasmalogens extracted from scallop were shown FIG. 7, FIG. 8a and FIG. 8b, respectively. Among the total 75 patients, 24% of them showed remarkable improvement, and 23% of them showed improvement. Among the total 58 patients with moderate AD, 32% of them showed remarkable improvement, and 21% of them showed improvement. Among the total 17 patients with severe AD, 28% of them showed improvement. The results indicate that the treatment significantly improved the patients with moderate AD.

Figure 9:
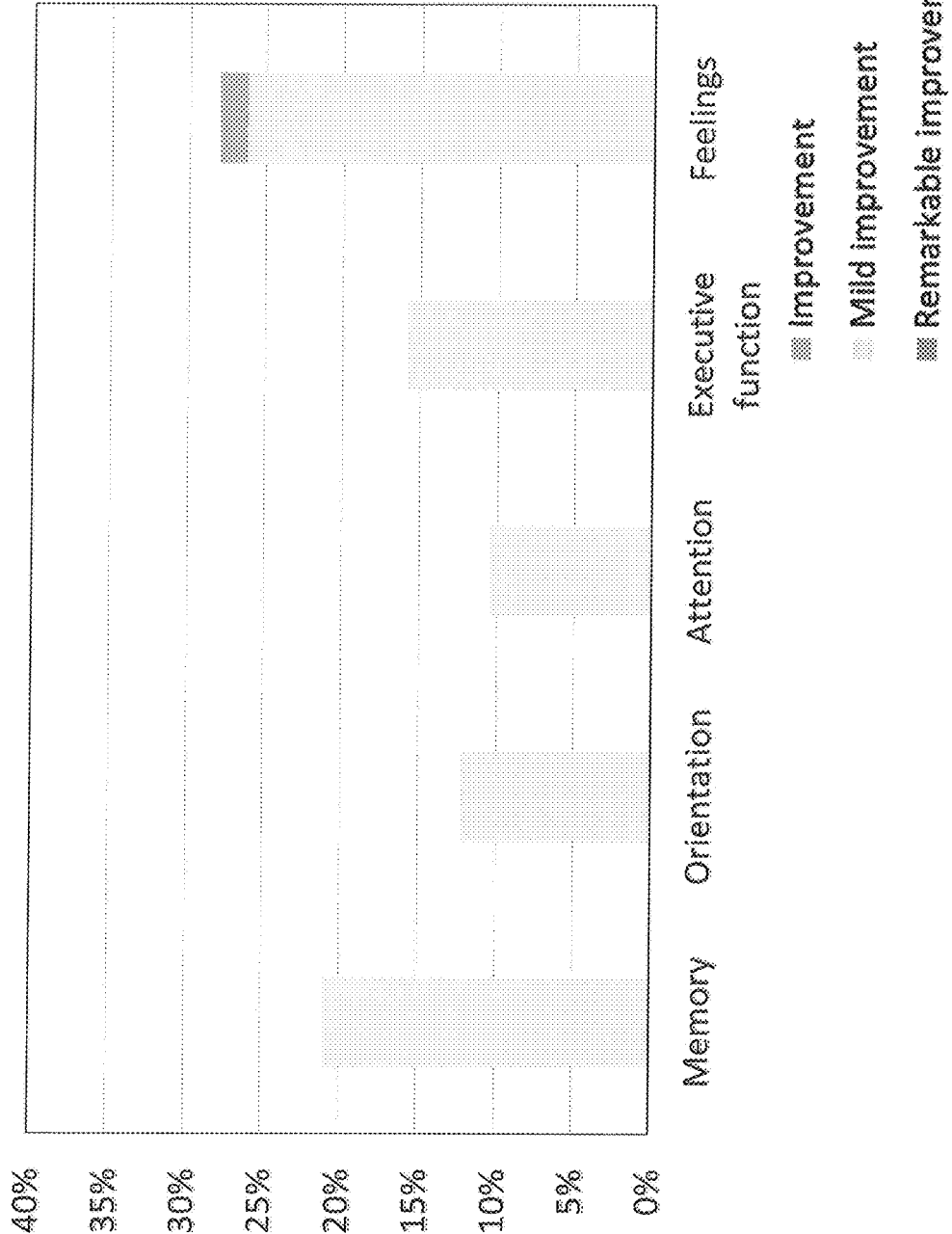
FIG. 9 depicts the evaluation of five mental functions (i.e., memory, orientation, attention, executive function, and feelings) of the patients with moderate AD and severe AD after three-month oral administration of plasmalogens extracted from scallop.
Figure 10:
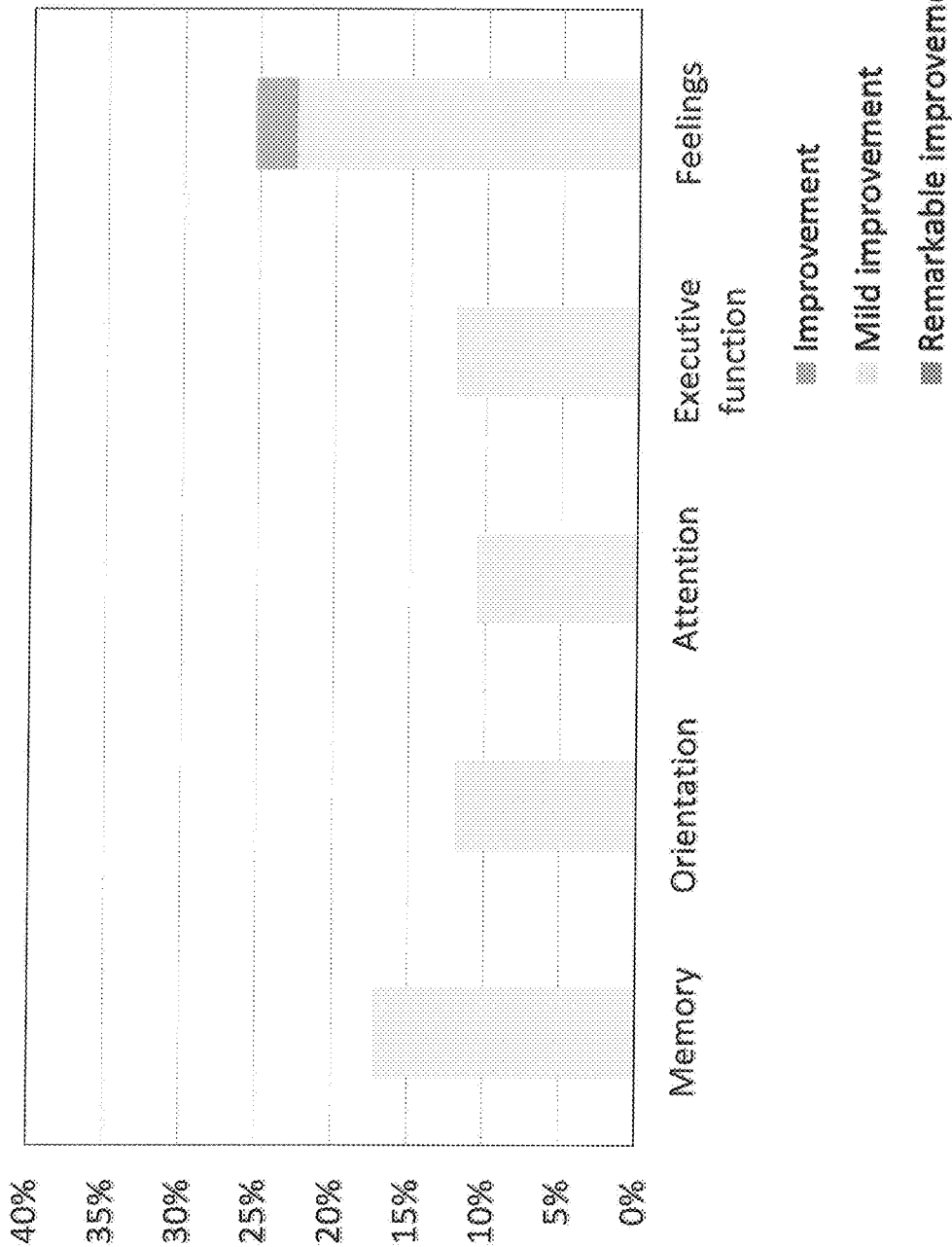
FIG. 10 depicts the evaluation of five mental functions (i.e., memory, orientation, attention, executive function, and feelings) of the patients with moderate AD after three-month oral administration of plasmalogens extracted from scallop.
Figure 11:
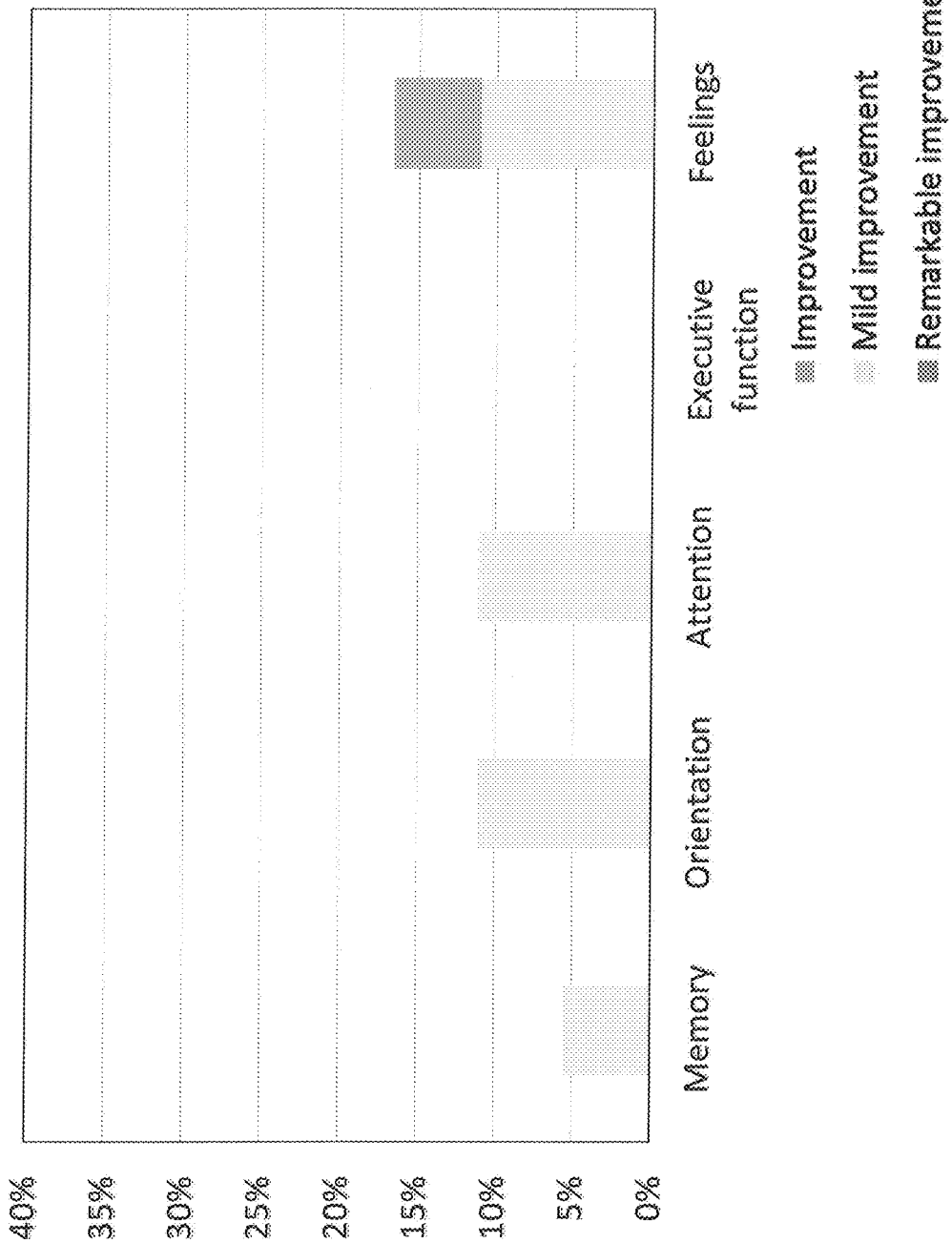
FIG. 11 depicts the evaluation of five mental functions (i.e., memory, orientation, attention, executive function, and feelings) of the patients with severe AD after three-month oral administration of plasmalogens extracted from scallop.
Figure 13B:
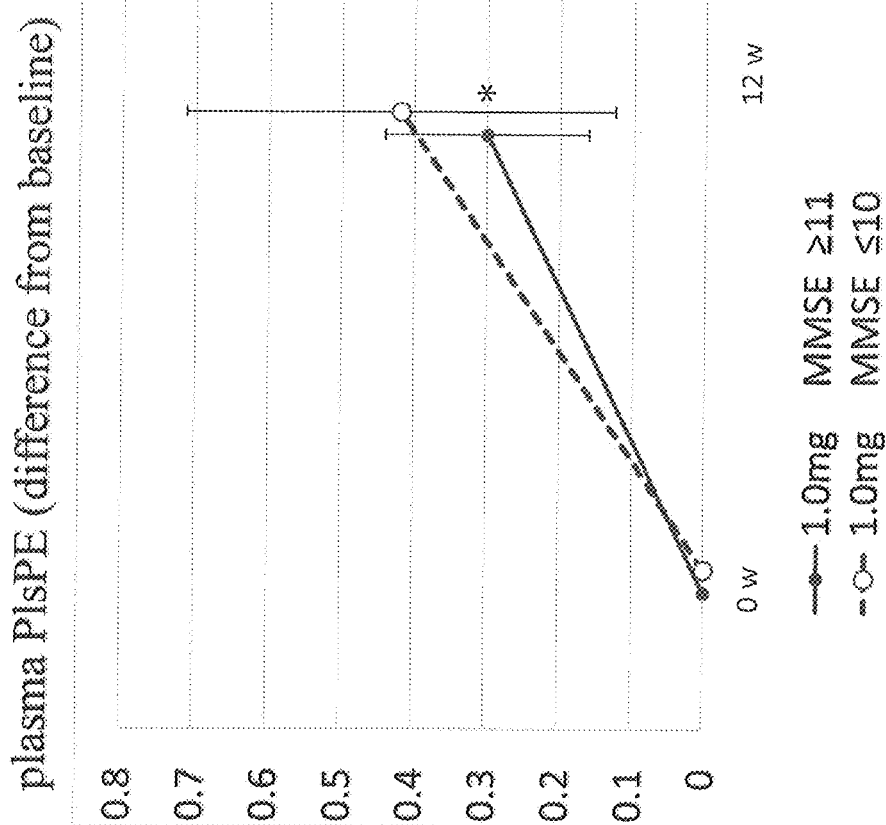
FIG. 13b depicts the mean changes of plasmalogens concentration with the baseline effect in plasma of the patients with moderate AD and severe AD after 12-week treatment.
Figure 13A:
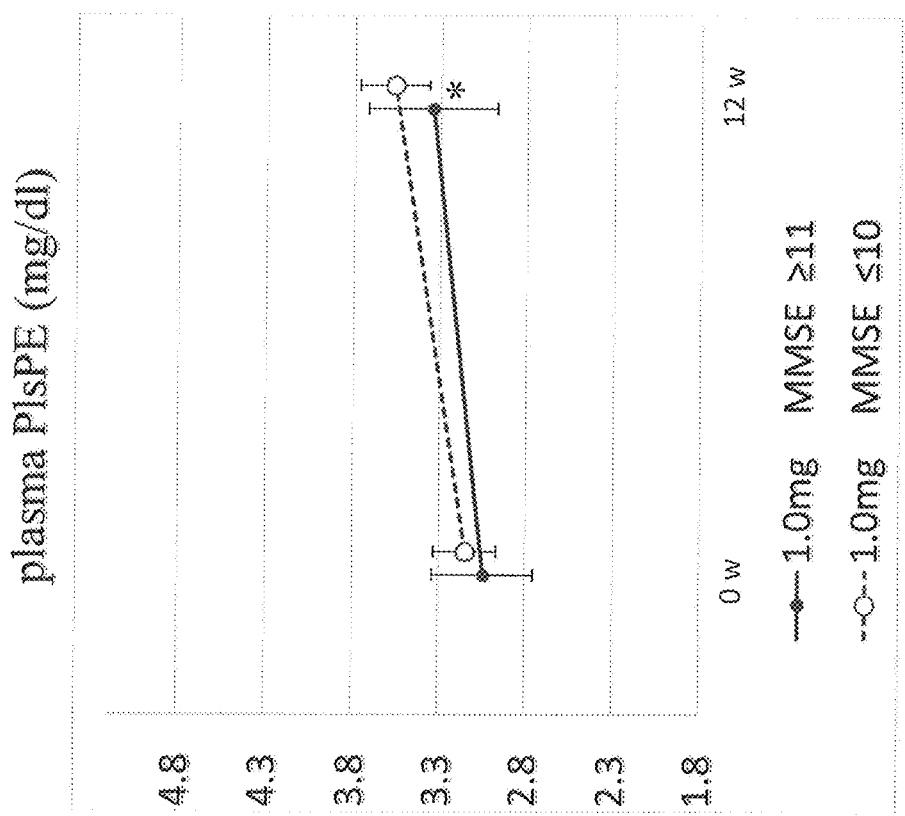
FIG. 13a depicts the mean changes of plasmalogens concentration without the baseline effect in plasma of the patients with moderate AD and severe AD after 12-week treatment.

The evaluation of five mental functions (i.e., memory, orientation, attention, executive function, feelings) of the total 75 patients, 58 patients with moderate AD and 17 patients with severe AD after three-month oral administration of plasmalogens extracted from scallop was showed in FIG. 9, FIG. 10 and FIG. 11, respectively.

The results indicate that the improvement for the patients with moderate AD was more remarkable than that for the patients with severe AD, and in particular in the improvement of motivation and emotion. These results indicate that oral administration of plasmalogens derived from scallop improves cognitive function in moderate AD.

Changes of the Concentration of Plasmalogens in Patients with Moderate to Severe AD after Oral Administration of Plasmalogens Extracted from Scallop The mean changes of plasmalogens concentration without and with the baseline effect in erythrocyte membrane and plasma of the patients with moderate AD and severe AD after 12-week treatment were shown in FIG. 12a, FIG. 12b, FIG. 13a and FIG. 13b, respectively.

The concentration of plasmalogens in erythrocyte membrane and plasma of the patients was significantly increased at the end point.

Example 4

Efficacy of Plasmalogens Extracted from Scallop in the Treatment of Insomnia 19 patients who had suffered from difficulty in getting sleep or arousal during sleep for three months or longer and had an Athens Insomnia Scale (AIS) five or higher (8 males, 11 females, aged 56.2±12.0) participated. They received orally 0.5 mg plasmalogens extracted from scallop every morning and evening for two weeks. No clinically significant side effects were observed.

The mean AIS scores were measured again after the two-week treatment. The AIS score exhibited a significant decrease from 11.5±3.7 to 6.4±3.4 ($P<0.0001$). There was no difference in effects between mild and moderate insomnia patients. Significant improvement was also seen in 9 patients who are on sleeping pills for a long time.

These results suggest that plasmalogens are effective in treating insomnia through a mechanism different from that of existing sleeping pills.

Example 5

Efficacy of Plasmalogens Extracted from Scallop in the Treatment of Parkinson's Disease (PD)

Fourteen patients with PD (6 male and 8 female, mean age 67.6 years±8.1) received 1 mg of scallop-derived plasmalogens every day for six months. No clinically significant side effects were observed. Symptoms of PD were assessed by Parkinson's disease questionnaire (PDQ-39), and changes in blood plasmalogens level were examined by LC/MS and HPLC method.

Mean changes in PDQ-39: A significant improvement was observed in the total scores of PDQ-39 six months after ingestion of plasmalogens ($P<0.018$). Especially, the dimensions of cognition, activities of daily living and bodily discomfort improved markedly.

Mean changes in blood plasmalogens level: Before plasmalogens ingestion, the levels of plasmalogens concentration in plasma and erythrocyte were significantly low compared to normal controls. These levels increased significantly to normal values six months after plasmalogens ingestion.

These results suggest that oral ingestion of plasmalogens may mitigate symptoms of PD with increasing levels of blood plasmalogens. Since the present antiparkinsonian drugs have multiple side effects, scallop-derived plasmalogens are greatly expected as a new drug for PD.

Example 6

Efficacy of Plasmalogens Extracted from Scallop in the Treatment of Mild Depression and Anxiety Disorder The Profile of Mood States (POMS) is a relatively new psychological rating scale used to assess transient, distinct mood states. The POMS measures six different dimensions of mood swings over a period of time. These include: Tension or Anxiety, Anger or Hostility, Vigor or Activity, Fatigue or Inertia, Depression or Dejection, and Confusion or Bewilderment. A five-point scale ranging from "not at all" to "extremely" is administered by experimenters to patients to assess their mood states.

Plasmalogens were given (0.5 mg/day) to 15 volunteers with mild depression and anxiety disorder (2 males, 13 females, aged 50.4±11.8) for 3 months. No clinically significant side effects were observed. POMS score was used to assess depression and anxiety disorder.

Significant improvements were observed in comparison of mean POMS scores before and after plasmalogens administration in the following categories: Tension or Anxiety (T-A) score decreased from 50.7±10.2 to 41.9±8.5, Depression (D) score decreased from 47.7±7.1 to 44.7±6.4, and Fatigue (F) score decreased from 48.5±8.92 to 42.7±7.76 ($p<0.001$, $p<0.017$, $p<0.002$).

It was suggested that plasmalogens are effective for mild depression and anxiety disorder.

Example 7

Efficacy of Plasmalogens Extracted from Scallop in the Treatment of Obesity

The body mass index (BMI) or Quetelet index is a value derived from the mass (weight) and height of an individual. The BMI is defined as the body mass divided by the square of the body height, and is universally expressed in units of kg/m, resulting from mass in kilograms and height in meters.

Plasmalogens were given (0.5 mg/day) to 6 overweight volunteers with body mass index (BMI) exceeding 25 (2 males, 4 females, aged 53.0±7.4) for 3 months and their weight changes were assessed. No clinically significant side effects were observed.

Their body weights significantly decreased from 74.2±17.1 kg before plasmalogens administration to 72.8±16.5 kg after administration ($p<0.01$). Their BMI significantly decreased from 29.2±5.7 to 28.6±5.5 ($p<0.01$).

It is suggested that plasmalogens are effective in treating obesity.

The invention claimed is:

1. A method of treating the Alzheimer's disease, Parkinson disease, or obesity, comprising administering to a subject in need thereof a therapeutically effective amount of ether phospholipids or a composition containing ether phospholipids,
wherein the ether phospholipids are derived from a method comprising:
(A) a step of extracting total lipids from bivalve tissue with a mixture of a non-polar organic solvent and a branched alcohol; and
(B) a step of reacting the total lipids obtained by the step (A) with phospholipase A1 to hydrolyze diacyl phospholipids mixed therein, followed by solvent partition to get a purified ether phospholipids, and
wherein the therapeutically effective amount of the ether phospholipids is about 0.5 mg to about 20 mg per dosage.

2. The method of claim 1, wherein the Alzheimer's disease is mild, moderate or severe Alzheimer's disease.

3. The method of claim 1, wherein the bivalve is a clam, a corbicula, a giant clam, a scallop, or an oyster.

4. The method of claim 1, wherein the tissue of a bivalve is an internal organ, a gonad, or muscle.

5. The method of claim 1, wherein the non-polar organic solvent is hexane, the branched alcohol is isopropanol, and a ratio of the volume of a non-polar organic solvent and the volume of a branched alcohol in the mixture is 3:2.

6. The method of claim 1, wherein the solvent partition is by hexane and isopropanol in step (B).

7. The method of claim 1, wherein the therapeutically effective amount of the ether phospholipids is about 0.5 mg to about 1 mg per dosage.

8. The method of claim 1, wherein the therapeutically effective amount of ether phospholipids is administered orally.

* * * * *